United States Patent
Hashimoto

(10) Patent No.: US 9,021,406 B2
(45) Date of Patent: Apr. 28, 2015

(54) PATTERN INSPECTION METHOD OF SEMICONDUCTOR DEVICE OPTICAL IMAGE

(71) Applicant: NuFlare Technology, Inc., Yokohama (JP)

(72) Inventor: Hideaki Hashimoto, Kanagawa (JP)

(73) Assignee: NuFlare Technology, Inc., Yokohama (JP)

(*) Notice: Subject to any disclaimer, the term of this patent is extended or adjusted under 35 U.S.C. 154(b) by 0 days.

(21) Appl. No.: 14/249,843

(22) Filed: Apr. 10, 2014

(65) Prior Publication Data
US 2014/0310662 A1  Oct. 16, 2014

(30) Foreign Application Priority Data
Apr. 12, 2013 (JP) .................................. 2013-083816

(51) Int. Cl.
G06F 17/50 (2006.01)
H01L 21/027 (2006.01)

(52) U.S. Cl.
CPC .......... *G06F 17/5081* (2013.01); *H01L 21/027* (2013.01)

(58) Field of Classification Search
CPC ................................ G06F 17/30; G06F 17/50
USPC .......................................................... 716/52
See application file for complete search history.

(56) References Cited

U.S. PATENT DOCUMENTS

2008/0319709 A1* 12/2008 Kurihara et al. ............... 702/155
2011/0176719 A1*  7/2011 Inoue et al. ................... 382/149
2013/0044205 A1*  2/2013 Matsumoto et al. ............ 348/86

FOREIGN PATENT DOCUMENTS

JP  3824542  9/2006

* cited by examiner

*Primary Examiner* — Vuthe Siek
*Assistant Examiner* — Mohammed Alam
(74) *Attorney, Agent, or Firm* — Oblon, McClelland, Maier & Neustadt, L.L.P.

(57) ABSTRACT

In accordance with one aspect of this invention, a pattern inspection method includes acquiring optical images regarding figure patterns arranged in each of frame regions, for each of the plurality of frame regions; measuring linewidth dimensions of the figure patterns, for each of the frame regions; operating an average value of each linewidth dimension shift between linewidth dimensions of figure patterns in a reference image corresponding to the frame region concerned and the linewidth dimensions of the figure patterns in the optical image, for each of the frame regions; extracting a specific frame from the frame regions by comparing the average value of the frame region concerned, with average values of frame regions around the frame region concerned, for each of the frame regions; and inspecting the specific frame for dimensional defects of linewidth dimensions.

16 Claims, 14 Drawing Sheets

Singular Point

PATTERN INSPECTION METHOD OF SEMICONDUCTOR DEVICE OPTICAL IMAGE

CROSS-REFERENCE TO RELATED APPLICATION

This application is based upon and claims the benefit of priority from prior Japanese Patent Application No. 2013-083816 filed on Apr. 12, 2013 in Japan, the entire contents of which are incorporated herein by reference.

BACKGROUND OF THE INVENTION

1. Field of the Invention

Embodiments described herein relate generally to a pattern inspection method. For example, embodiments described herein relate generally to an inspection apparatus and method that inspect a pattern by acquiring an optical image of a pattern image through irradiation of laser light or an electron beam.

2. Related Art

In recent years, with increasingly higher degrees of integration and larger capacities of large-scale integration circuits (LSI), circuit line widths demanded for semiconductor devices become increasingly narrower. Such semiconductor devices are fabricated by exposing and transferring a pattern onto a wafer by step-and-repeat equipment, the so-called stepper, to form a circuit using an original pattern (also called a mask or reticle; hereinafter, collectively called a mask) in which a circuit pattern is formed. Thus, to manufacture a mask for transferring such a fine circuit pattern to a wafer, a pattern writing apparatus capable of writing a fine circuit pattern and using an electron beam is used. By using such a pattern writing apparatus, a pattern circuit may directly be written onto a wafer. Alternatively, the development of a laser beam writing apparatus that writes by using a laser beam, in addition to the electron beam, is attempted.

The improvement of yield is indispensable for manufacturing LSI requiring a large amount of manufacturing costs. However, as is typically shown by DRAM (Random Access Memory) of 1 gigabit or so, patterns constituting LSI are in transition from the order of submicron to that of nanometer. One of the major causes that decrease the yield is a pattern defect of the mask used when a superfine pattern is exposed and transferred onto a semiconductor wafer by photolithography technology. With increasingly finer LSI pattern dimensions formed on the semiconductor wafer in recent years, dimensions that need to be detected as pattern defects are also extremely small. Therefore, a pattern inspection apparatus that inspects for defects of a transfer mask used for manufacturing LSI needs to be made more precise.

As an inspection method, a method of conducting an inspection by comparing an optical image obtained by capturing an image of a pattern formed on a target object like a lithography mask in a predetermined magnification by using an enlarging optical system with design data or an optical image obtained by capturing an image of the same pattern on the target object is known. Examples of the pattern inspection method include the die to die inspection that compares optical image data obtained by capturing an image of the same pattern in different places on the same mask and the die to database inspection that compares design image data (reference image) generated by inputting into an inspection apparatus pattern writing data (design pattern data) converted into the apparatus input format to be input into a pattern writing apparatus when a pattern is written using pattern-designed CAD data as a mask and an optical image to be measured data obtained by capturing the pattern. In such inspection methods of the inspection apparatus, a target object is placed on a stage and an inspection is conducted by scanning the target object with a luminous flux as the stage moves. The target object is irradiated with a luminous flux by a light source and an illumination optical system. Light transmitted through or reflected by the target object forms an image on a sensor via an optical system. The image captured by the sensor is sent to a comparator as measured data. After images are aligned, the comparator compares the measured data and reference data according to an appropriate algorithm and determines that there is a pattern defect if the measured data and the reference data do not match.

In such a pattern defect (shape defect) inspection, detection of pattern linewidth (CD) defects (CD error inspection) is also demanded. In the CD error inspection, the pattern linewidth in an obtained image is measured and a difference from design data is determined to check whether the difference of the linewidth is within a permitted value. Also, an inspection method that, instead of conducting a CD error inspection of each pattern for the entire mask surface, detects a linewidth defective region as a CD error by measuring the linewidth of a pattern in an image obtained for each set region, determining a difference from design data, and comparing the average value of differences of all linewidths in the region and a threshold is proposed (see Japanese Patent No. 3824542, for example).

With increasing micropatterning of late, micropatterning technology progresses in the pattern transfer using a mask. For example, micropatterning processes by double patterning and further, multiple patterning like triple, quadruple, . . . are increasingly used. In a micropatterning process based on superposition, the linewidth (CD) of a pattern itself formed on a mask does not become narrower even if the final transferred pattern becomes finer and thus, shape defects like irregularities of a pattern do not necessarily become smaller in proportion to micropatterning. Regarding the precision of the linewidth (CD), on the other hand, superposition precision is affected and thus, the permitted value of a CD error becomes smaller in proportion to micropatterning or multiplexing. Therefore, requirements for the CD error inspection become more stringent in proportion to micropatterning. However, the detection limit of a CD error by deep ultraviolet (DUV) light used as the inspection light is near its limit due to the pixel size and optical resolution.

The permitted value of a CD error becomes smaller, as described above, in proportion to micropatterning. However, as described above, the detection limit of a CD error by deep ultraviolet (DUV) light used for inspection light is near its limit. If CD of patterns of the entire mask surface is inspected by using a conventional inspection apparatus and making the determination threshold stricter (smaller), the number of patterns erroneously determined to be CD errors becomes huge, which makes the method an unrealistic inspection method. If the determination threshold is made smaller in an inspection method of detecting an abnormal linewidth region as a CD error, the number of regions erroneously determined to be abnormal linewidth regions becomes huge. If internal patterns of all regions determined to be CD errors should be checked, the amount of checks and the time needed for checks become huge, which makes the method an unrealistic inspection method. Thus, both methods have their limits to making the determination threshold smaller. Therefore, there exists a problem that it is difficult to conduct a high-precision CD error inspection accompanying increasing micropatterning.

BRIEF SUMMARY OF THE INVENTION

In accordance with one aspect of this invention, a pattern inspection method includes:

acquiring a plurality of optical images regarding a plurality of figure patterns arranged in each of a plurality of frame regions obtained by virtually dividing an inspection region of a target object, for each of the plurality of frame regions;

measuring linewidth dimensions of the plurality of figure patterns in an optical image of the plurality of optical images regarding a frame region concerned, for each of the plurality of frame regions;

operating an average value of each linewidth dimension shift between linewidth dimensions of a plurality of figure patterns in a reference image corresponding to the frame region concerned and the linewidth dimensions of the plurality of figure patterns in the optical image regarding the frame region concerned, for each of the plurality of frame regions;

extracting a specific frame from the plurality of frame regions by comparing the average value of the frame region concerned, with average values of frame regions around the frame region concerned, for each of the plurality of frame regions; and inspecting the specific frame for dimensional defects of linewidth dimensions of a plurality of figure patterns arranged in the specific frame.

In accordance with other aspects of the invention, a pattern inspection method includes:

acquiring an optical image of a plurality of figure patterns arranged in each of a plurality of frame regions obtained by virtually dividing an inspection region of a target object for each of the plurality of frame regions;

measuring linewidth dimensions of the plurality of figure patterns in the optical image regarding a frame region concerned for each of the plurality frame regions;

creating a histogram of linewidth dimension shift using each linewidth dimension shift between linewidth dimensions of a plurality of figure patterns in a reference image corresponding to the frame region concerned and the linewidth dimensions of the plurality of figure patterns in the optical image regarding the frame region concerned for each of the plurality frame regions;

extracting a frame region for which a histogram having a linewidth dimension shift amount deviating from a normal distribution is created as a specific frame from the plurality of frame regions; and inspecting the specific frame for dimensional defects of the linewidth dimensions of a plurality of figure patterns arranged in the specific frame.

DETAILED DESCRIPTION OF THE INVENTION

In the embodiments below, methods capable of conducting a CD error inspection with high precision while making the determination threshold stricter will be described.

Embodiment 1

Figure 1:
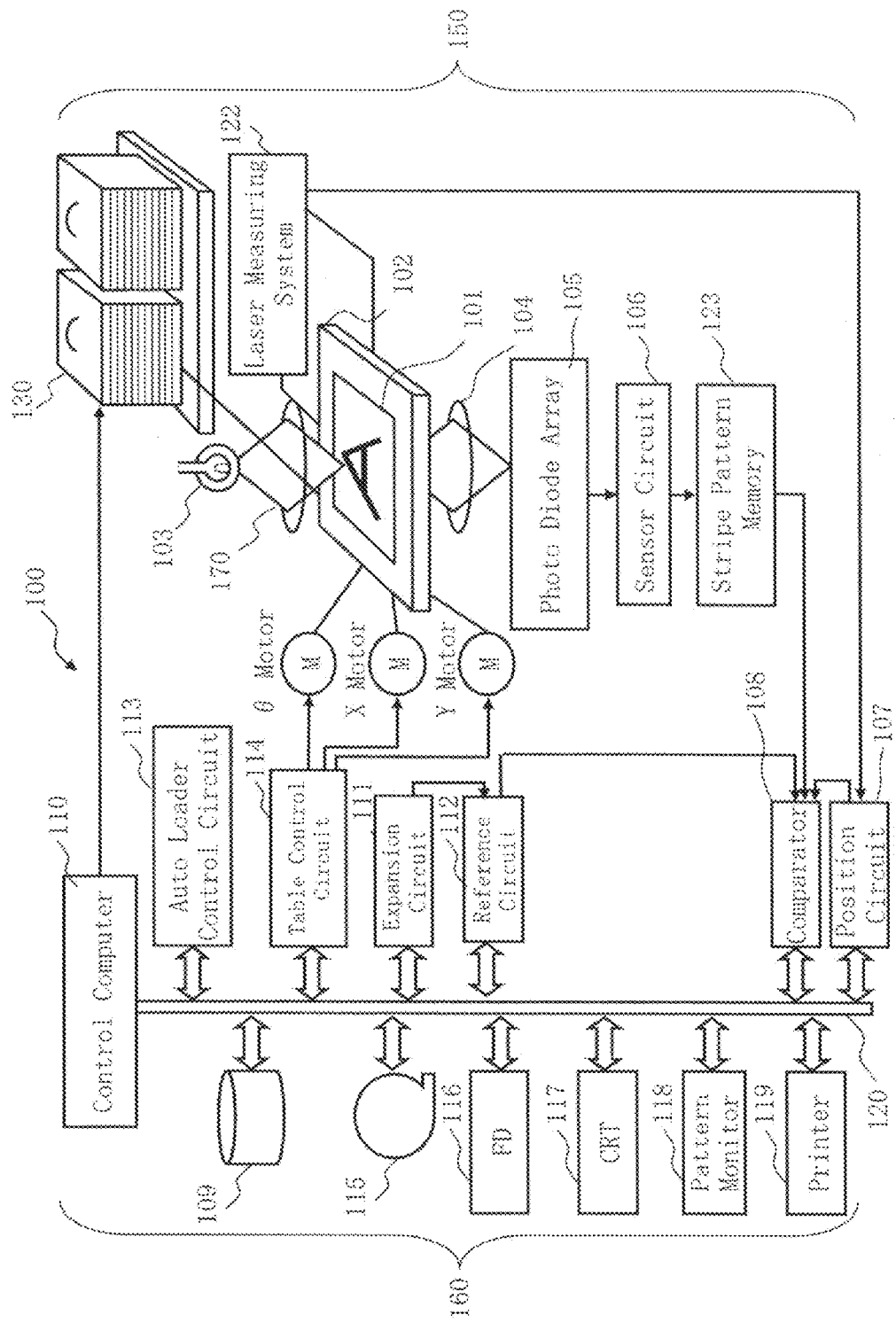
FIG. 1 is a schematic diagram showing the configuration of a pattern inspection apparatus according to Embodiment 1.

FIG. 1 is a schematic diagram showing a configuration of a pattern inspection apparatus according to Embodiment 1. In FIG. 1, an inspection apparatus 100 that inspects for defect of a pattern formed on a target object, for example, a mask includes an optical image acquisition unit 150 and a control system circuit 160 (control unit).

The optical image acquisition unit 150 includes a light source 103, an illumination optical system 170, an XYθ table 102 arranged movably, an enlarging optical system 104, a photo diode array 105 (an example of a sensor), a sensor circuit 106, a stripe pattern memory 123, and a laser measuring system 122. A target object 101 is arranged on the XYθ table 102. The target object 101 includes, for example, a photomask for exposure that transfers a pattern to a wafer. The photomask has a pattern including a plurality of figures to be an inspection target formed therein. The target object 101 is arranged on the XYθ table 102, for example, with the pattern formation surface directed downward.

In the control system circuit 160, a control computer 110 to be a computer is connected to a position circuit 107, a comparator 108, an expansion circuit 111, a reference circuit 112, an auto loader control circuit 113, a table control circuit 114, a magnetic disk drive 109, a magnetic tape drive 115, a flexible disk drive (FD) 116, a CRT 117, a pattern monitor 118, and a printer 119 via a bus 120. In addition, a sensor circuit 106 is connected to a stripe pattern memory 123 and the stripe pattern memory 123 is connected to the comparator 108. The XYθ table 102 is driven by an X-axis motor, a Y-axis motor, and a Z-axis motor. The XYθ table 102 is an example of a stage.

In the inspection apparatus 100, an inspection optical system of high magnification is constituted by the light source 103, the XYθ table 102, the illumination optical system 170, the enlarging optical system 104, the photo diode array 105, and the sensor circuit 106. The XYθ table 102 is driven by the table control circuit 114 under the control of the control computer 110. The XYθ table 102 is made movable by a driving system like a 3-axis (X-Y-θ) motor driving in the X direction, the Y direction, and θ direction. For example, step motors can be used as these X motor, Y motor, and θ motor. The XYθ table 102 is movable in the horizontal direction and the rotation direction by the motor of each of the xyθ axes. Then, the movement position of the XYθ table 102 is measured by the laser measuring system 122 and supplied to the position circuit 107.

In FIG. 1, a portion of the configuration needed to describe Embodiment 1 is shown. It is needless to say that other configurations that are normally needed for the inspection apparatus 100 may be included.

Figure 2:
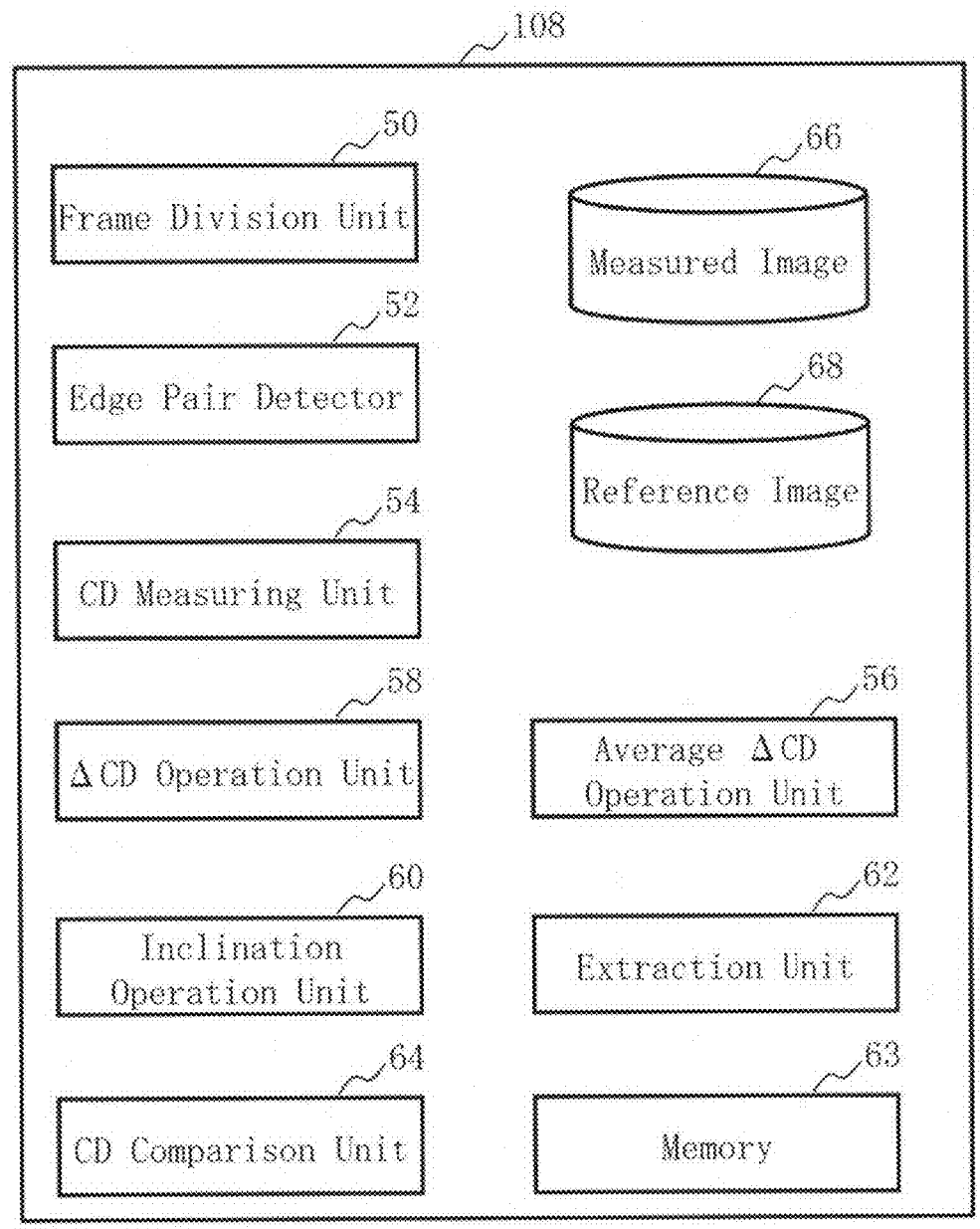
FIG. 2 is a diagram showing an internal configuration of a comparator according to Embodiment 1.

FIG. 2 is a diagram showing an internal configuration of a comparator according to Embodiment 1. In FIG. 2, a frame division unit 50, an edge pair detector 52, a CD measuring unit 54, an average ΔCD operation unit 56, a Δ CD operation unit 58, an inclination operation unit 60, an extraction unit 62, a CD comparison unit 64, and memories 63, 66, 68 are arranged inside the comparator 108. Functions such as the frame division unit 50, the edge pair detector 52, the CD measuring unit 54, the ΔCD operation unit 58, the average ΔCD operation unit 56, the inclination operation unit 60, the extraction unit 62, and the CD comparison unit 64 may be configured by software such as programs. Alternatively, such functions may be configured by hardware such as an electronic circuit. Alternatively software and hardware may be combined. Input data needed for the comparator 108 or an operation result is each time stored in the memory 63.

Figure 3:
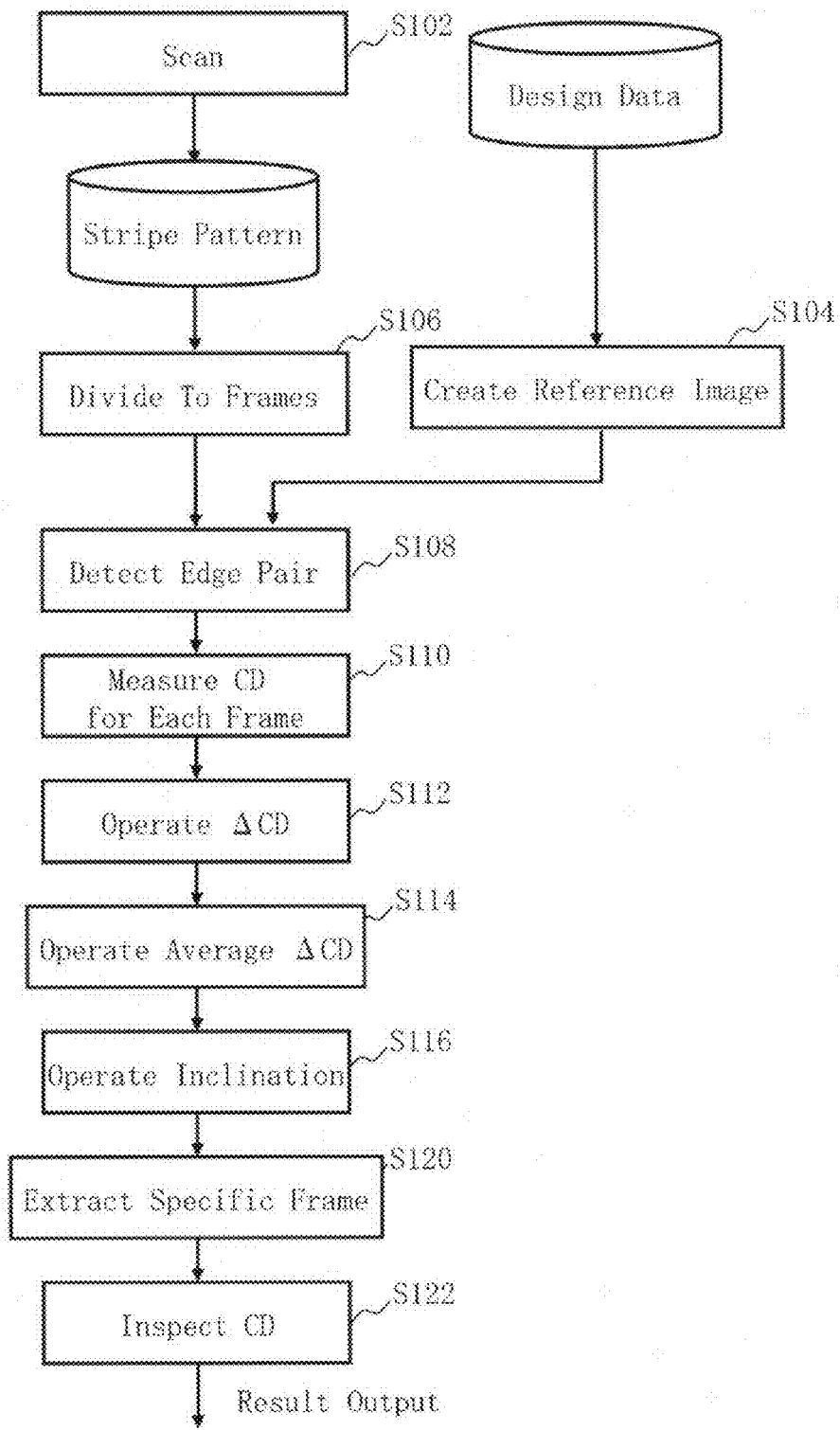
FIG. 3 is a flow chart showing principal processes of a pattern inspection method according to Embodiment 1.

FIG. 3 is a flow chart showing principal processes of a pattern inspection method according to Embodiment 1. In FIG. 3, a pattern inspection method according to Embodiment 1 executes a series of processes including a scan process (S102), a reference image creation process (S104), a frame division process (S106), an edge pair detection process (S108), a CD measuring process (S110), a ΔCD operation process (S112), an average ΔCD operation process (S114), an inclination operation process (S116), a specific frame extraction process (S120), and a CD inspection process (S122).

As the scan process (S102) (optical image acquisition process), the optical image acquisition unit 150 acquires an optical image of the target object 101 on which a pattern is formed. A more specific operation is as described below.

The pattern formed on the target object 101 is irradiated with laser light (for example, DUV light) of a wavelength in the ultraviolet region or less to be inspection light from the appropriate light source 103 via the illumination optical system 170. The light having passed through the photomask 101 enters the photo diode array 105 (an example of a sensor) via the enlarging optical system 104 to form an optical image there. As the photo diode array 105, for example, a TDI (Time Delay Integration) sensor or the like can suitably be used.

Figure 4:
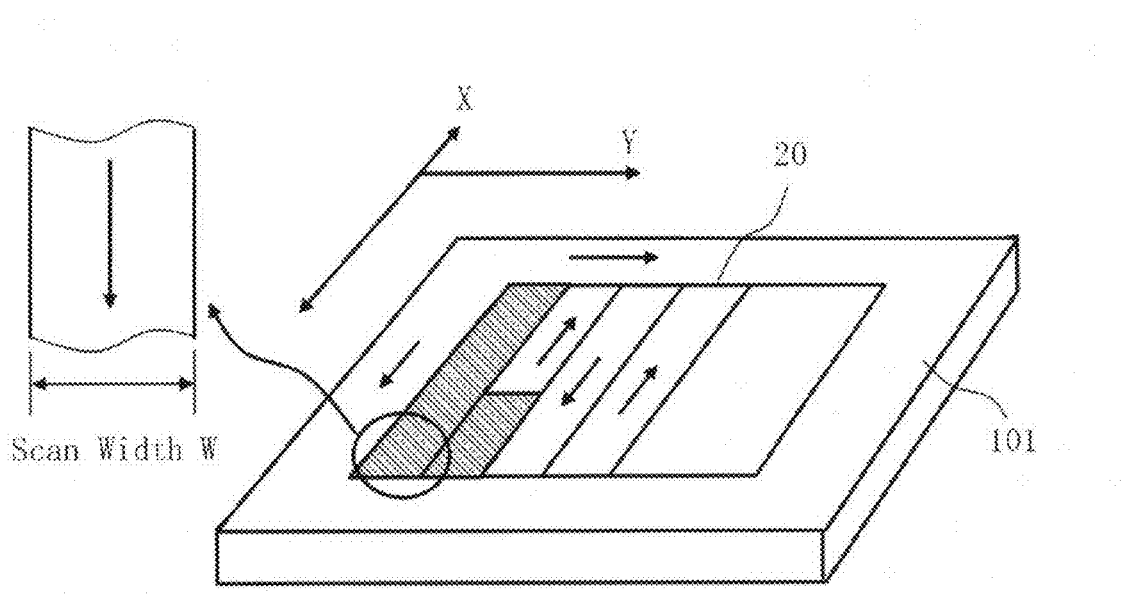
FIG. 4 is a conceptual diagram illustrating an inspection region in Embodiment 1.

FIG. 4 is a conceptual diagram illustrating an inspection region in Embodiment 1. As shown in FIG. 4, an inspection region 10 (whole inspection region) of the target object 101 is virtually divided into a plurality of inspection stripes 20 in a thin rectangular shape of a scan width W, for example, in the Y direction. Then, the inspection apparatus 100 acquires an image (stripe region image) from each of the inspection stripes 20. Laser light is used to capture an image of a figure pattern arranged in each of the inspection stripes 20 in the longitudinal direction (X direction) of the stripe region. As the XYθ table 102 moves, an optical image is acquired while the photo diode array 105 continuously moves relatively in the X direction. The photo diode array 105 continuously captures an optical image of the scan width W as shown in FIG. 4. In other words, the photo diode array 105 as an example of the sensor captures an optical image of a pattern formed on the target object 101 by using inspection light while moving relatively with respect to the XYθ table 102. In Embodiment 1, after an optical image of the one inspection stripe 20 is captured, an optical image of the scan width W is similarly captured continuously by moving to the position of the next inspection stripe 20 in the Y direction, this time in the opposite direction. That is, image capturing is repeated in the forward (FWD) and backward (BWD) directions in which the direction of scanning is changed in the opposite direction each time.

The direction of imaging is not limited to the repetition of forward (FWD) and backward (BWD). Images may be captured in one direction. For example, FWD-FWD may be repeated. Alternatively, BWD-BWD may be repeated.

The image of a pattern formed on the photo diode array 105 is photoelectrically converted by each photoreceptor of the photo diode array 105 and further A/D (analog/digital) converted by the sensor circuit 106. Then, pixel data is stored in the stripe pattern memory 123 for each of the inspection stripes 20. When such pixel data (stripe region image) is obtained by capturing, a dynamic range in which a case where 100% of the amount of illumination light is incident is set as the maximum gray level is used as the dynamic range of the photo diode array 105. Subsequently, the stripe region image is sent to the comparator 108 together with data output from the position circuit 107 and indicating the position of the photomask 101 on the XYθ table 102. Measured data (pixel data) is, for example, unsigned 8-bit data and represents the gray level of brightness (amount of light) of each pixel. The stripe region image output into the comparator 108 is stored in the memory 66.

As the reference image creation process (S104), a reference image corresponding to a frame image described later is created. A more specific operation is as described below. First, the expansion circuit 111 reads information of a design pattern of a pattern formed on the target object 101 from the magnetic disk drive 109 through the control computer 110 and converts the read design pattern into binary or multi-valued image data, which is sent to the reference circuit 112.

Figures contained in the design pattern use a rectangle or a triangle as a basic figure and figure data defining the shape, size, position and the like of each pattern figure by information, for example, coordinates (x, y) in the reference position of the figure, lengths of sides, and the figure code as an identifier identifying the kind of figure such as the rectangle and triangle is stored.

When information of a design pattern to be such figure data is input into the expansion circuit 111, the expansion circuit 111 expands the information into data of each figure and interprets the figure code indicating the figure shape of the figure data, figure dimensions and the like. Then, the expansion circuit 111 expands and outputs binary or multi-valued design image data as a pattern arranged in a square in units of grid of predetermined quantization dimensions. In other words, the expansion circuit 111 reads design pattern data, operates the occupancy rate occupied by figures in the design pattern for each square created by virtually dividing an inspection region into squares in units of predetermined dimensions, and outputs n-bit occupancy rate data. For example, one square is suitably set as one pixel. If one pixel is given resolving power of $1/2^8(=1/256)$, the expansion circuit 111 assigns 1/256 small regions for the region of figures arranged in the pixel to operate an occupancy rate in the pixel. Then, the expansion circuit 111 outputs the occupancy rate as 8-bit occupancy rate data to the reference circuit 112.

Next, the reference circuit 112 performs appropriate filter processing on design image data as image data of the sent figure.

Figure 5:
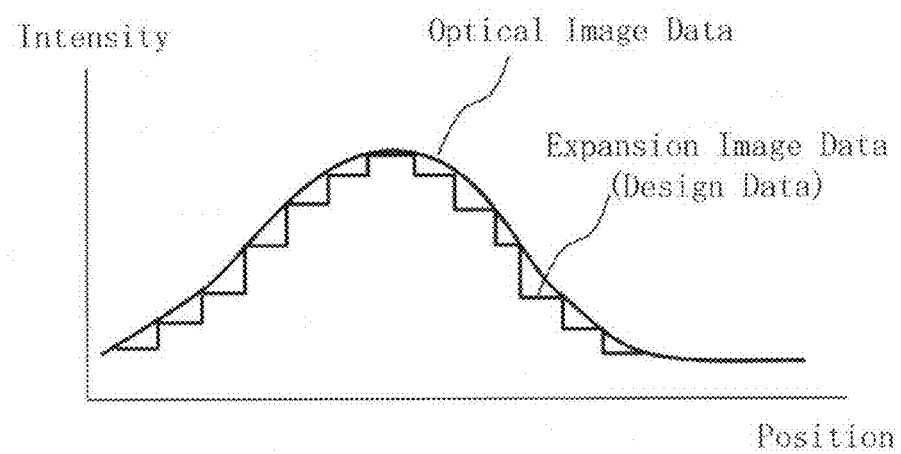
FIG. 5 is a diagram illustrating filter processing in Embodiment 1.

FIG. 5 is a diagram illustrating filter processing in Embodiment 1. Because measured data as an optical image obtained from the sensor circuit 106 is in a state in which a filter acts due to resolution characteristics of the enlarging optical system 104 or an aperture plate effect of the photo diode array 105, in other words, in an analog state of continuous change, design image data as image data on the design side in which the image density (multilevel value) is a digital value can be matched to measured data by performing filter processing thereon. In this manner, a reference image to be compared with an optical image is created. The created reference image is output to the comparator 108 and the reference image output to the comparator 108 is stored in the memory 68.

As the frame division process (S106), the frame division unit 50 reads a stripe region image from the memory 66 and divides the stripe region image into a plurality of frame images in a predetermined size (for example, the same width as the scan width W) in the x direction. For example, the stripe region image is divided into frame images of 512×512 pixels.

Figure 6:
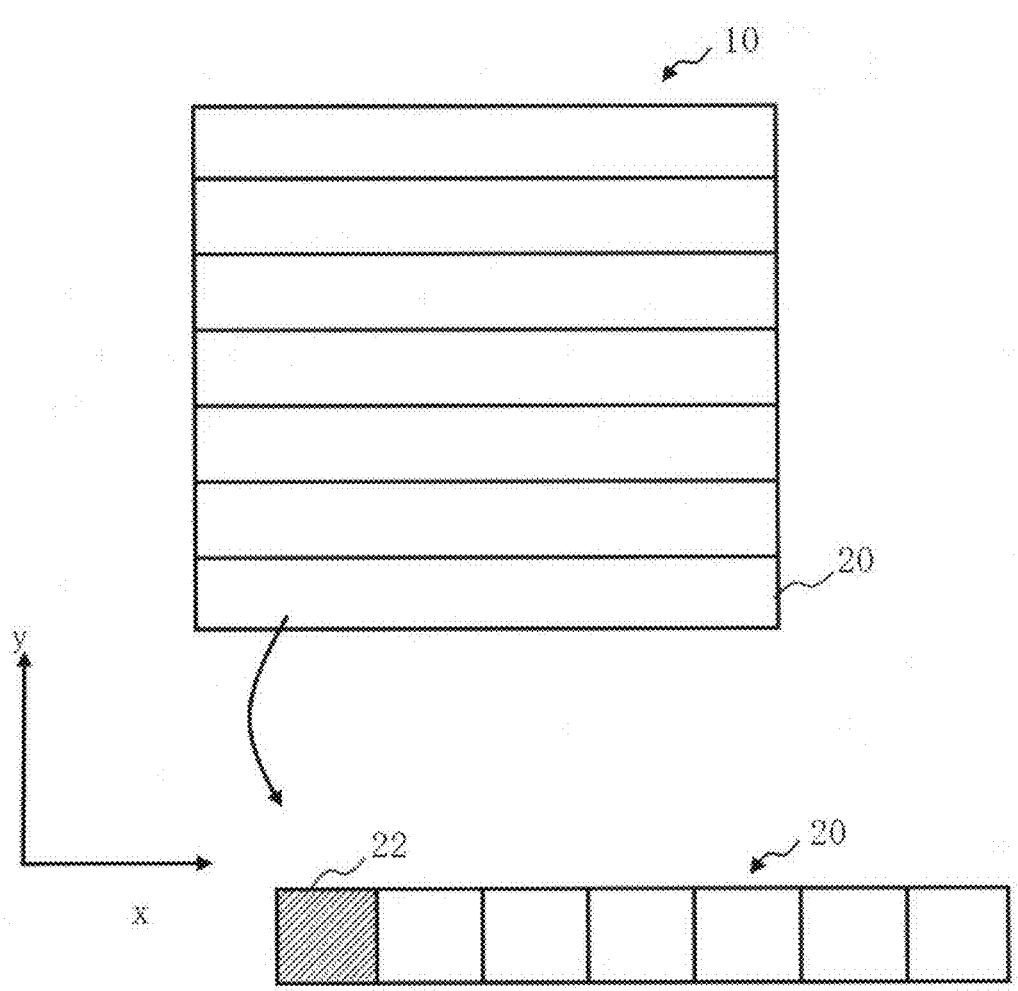
FIG. 6 is a diagram illustrating a frame region in Embodiment 1.

FIG. 6 is a diagram illustrating a frame region in Embodiment 1. In FIG. 6, each of the inspection stripes 20 obtained by virtually dividing the inspection region 10 of the target object 101 in a thin rectangular shape in the y direction is divided into a plurality of frame regions 22 in the x direction, for example, in the same width as the scan width W. In other words, the inspection region 10 of the target object 101 is virtually divided into the plurality of frame regions 22. Thus, by dividing the stripe region image of each of the inspection stripes 20 in the x direction, for example, in the same width as the scan width W, a frame image (optical image) of a plurality of figure patterns arranged in each of the frame regions 22 is acquired.

As the edge pair detection process (S108), the edge pair detector 52 recognizes the position of an edge portion (peripheral side) of a pattern from the corresponding reference image for each frame image to detect an edge portion in the frame image to be a pair of the pattern edge portion of the reference image. Then, an edge pair formed of edges of both ends (both peripheral sides) constituting CD of a pattern is detected in, for example, pixel units. Thus, for example, in a pattern in which a peripheral side extends in the y direction, a pair is detected for each pixel on the peripheral side. Here, an edge pair is detected also for a pattern in which a peripheral side extends in the x direction.

As the CD measuring process (S110), the CD measuring unit 54 measures linewidth dimensions CD of a plurality of figure patterns in a frame image (optical image) of each frame region.

Figure 7A:
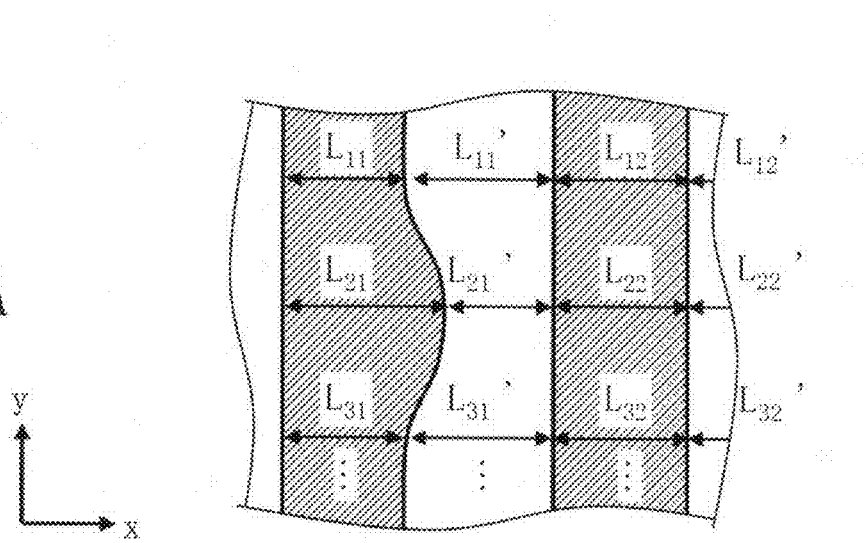
FIGS. 7A and 7B are diagrams illustrating a method of measuring CD in Embodiment 1.
Figure 7B:
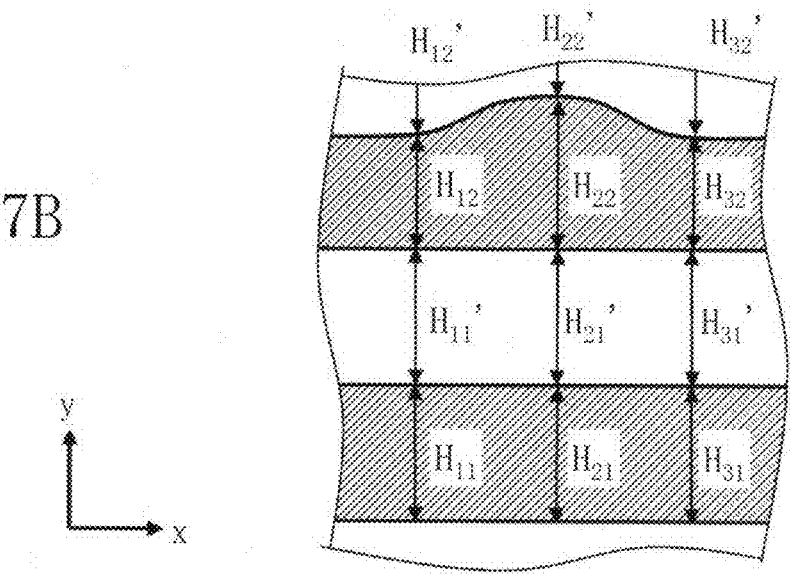

FIGS. 7A and 7B are diagrams illustrating a method of measuring CD in Embodiment 1. In FIGS. 7A and 7B, portions of frame images are shown. In the example of FIG. 7A, line & space patterns arranged in the x direction are shown as a plurality of patterns captured in a frame image. Here, a line portion (black portion) is indicated by oblique lines. In addition to the linewidth of such a line portion, the linewidth of a space portion (white portion) is present in CD to be measured. Here, black portions and white portions are measured separately. In FIG. 7A, $L_{11}, L_{12}, \ldots$ are measured in the x direction in the same position in the y direction as linewidths of line portions (black portions). Similarly, the $L'_{11}, L'_{12} \ldots$ are measured in the x direction as linewidths of space portions (white portions). Then, in a position shifted by one pixel in the y direction, $L_{21}, L_{22}, \ldots$ are measured in the x direction in the same position in the y direction as linewidths of line portions (black portions). Similarly, the $L'_{21}, L'_{22}, \ldots$ are measured in the x direction as linewidths of space portions (white portions). Then, in a position shifted by one pixel in the −y direction, $L_{31}, L_{32}, \ldots$ are measured in the x direction in the same position in the y direction as linewidths of line portions (black portions). Similarly, the $L'_{31} L'_{32}, \ldots$ are measured in the x direction as linewidths of space portions (white portions). In this manner, the linewidth of an edge pair detected in pixel units is measured.

In the example of FIG. 7B, line & space patterns arranged in the y direction are shown. Here, a line portion (black portion) is indicated by oblique lines. In addition to the linewidth of such a line portion, the linewidth of a space portion (white portion) is present in CD to be measured. Here, black portions and white portions are measured separately. In FIG. 7B, $H_{11}, H_{12}, \ldots$ are measured in the y direction in the same position in the x direction as linewidths of line portions (black portions). Similarly, the $H'_{11}, H'_{12}, \ldots$ are measured in the y direction as linewidths of space portions (white portions). Then, in a position shifted by one pixel in the x direction, $H_{21}, H_{22}, \ldots$ are measured in the y direction in the same position in the x direction as linewidths of line portions (black portions). Similarly, the $H'_{21}, H'_{22}, \ldots$ are measured in the y direction as linewidths of space portions (white portions). Then, in a position shifted by one pixel in the x direction, $H_{31}, H_{32}, \ldots$ are measured in the y direction in the same position in the x direction as linewidths of line portions (black portions). Similarly, the $H'_{21}, H'_{32}, \ldots$ are measured in the y direction as linewidths of space portions (white portions). In this manner, the linewidth of an edge pair detected in pixel units is measured.

Line & space patterns are shown in the examples of FIGS. 7A and 7B, but the pattern is not limited to such examples. Measurements can be made similarly for a plurality of other patterns. CD measurements may be made by regarding each pattern portion as a black portion and a space between neighboring pattern portions as a white portion.

In this manner, for each frame image, CD in the x direction and CD in the y directions are measured for black portions and CD in the x direction and CD in the y directions are measured for white portions.

As the $\Delta CD$ operation process (S112), the $\Delta CD$ operation unit 58 operates each linewidth dimension shift $\Delta CD$ (linewidth difference) between linewidth dimensions of a plurality of figure patterns in a reference image corresponding to each frame region and linewidth dimensions of a plurality of figure patterns in a frame image of the frame region. Thus, for each frame image, $\Delta CD$ in the x direction and $\Delta CD$ in the y directions are measured for black portions and $\Delta CD$ in the x direction and $\Delta CD$ in the y directions are measured for white portions.

As the average $\Delta CD$ operation process (S114), the average $\Delta CD$ operation unit 56 operates an average value (average $\Delta CD$) of each linewidth dimension shift $\Delta CD$ (linewidth difference) of the plurality of figure patterns in the frame image of the frame region for each frame region. An average value is determined by adding all $\Delta CD$ in the x direction of black portions. Similarly, an average value is determined by adding all $\Delta CD$ in the y direction of black portions. Similarly, an average value is determined by adding all $\Delta CD$ in the x direction of white portions. Similarly, an average value is determined by adding all $\Delta CD$ in the y direction of white portions. In this manner, the average $\Delta CD$ for each region is determined.

Figure 8A:
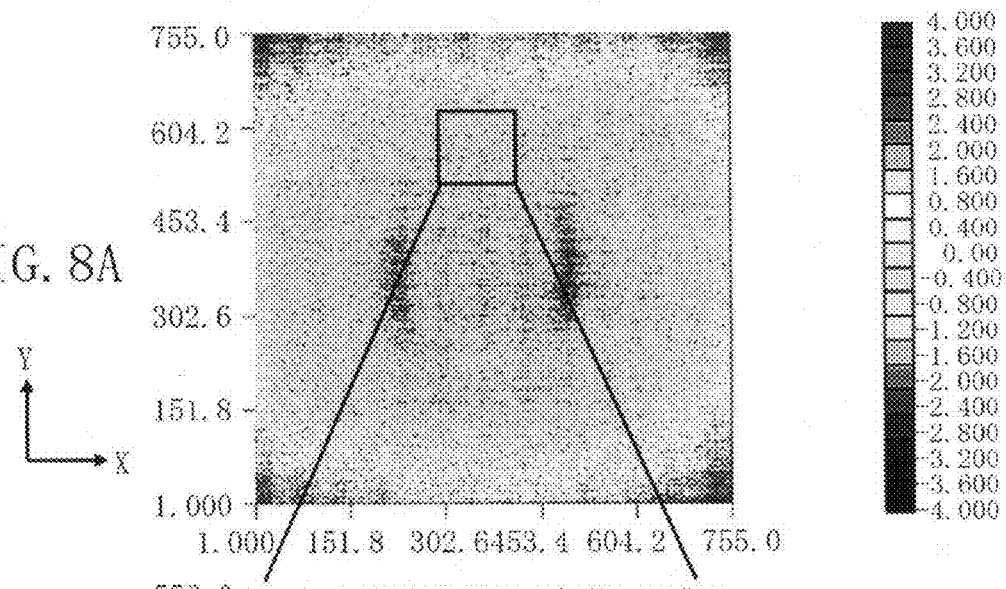
FIGS. 8A to 8C are diagrams showing an example of the frame region and changes of average ΔCD in Embodiment 1.
Figure 8B:
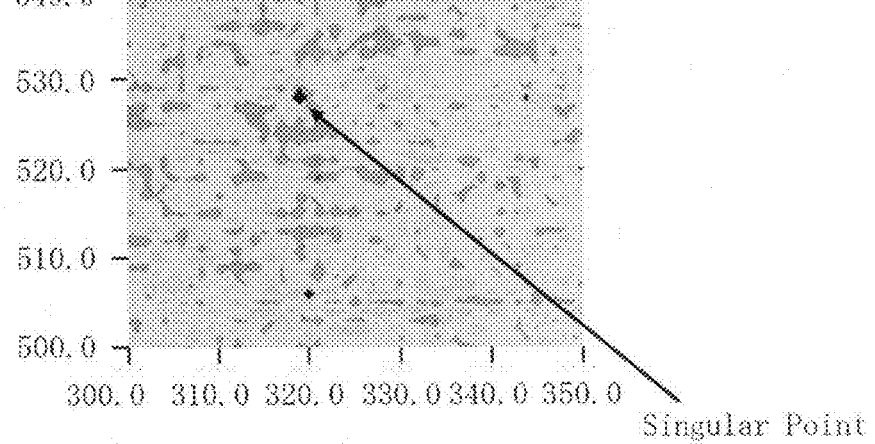
Figure 8C:
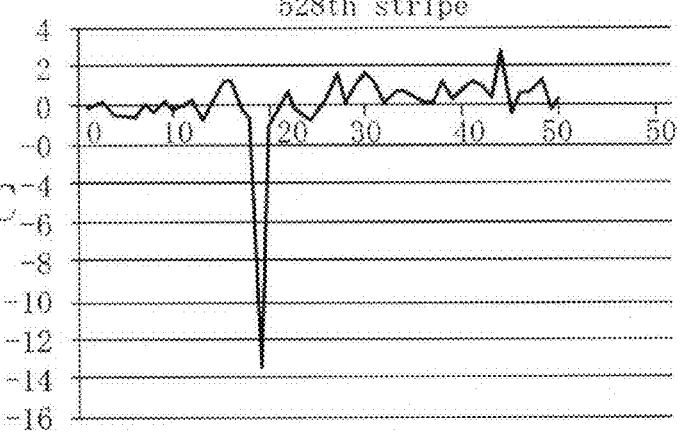

FIGS. 8A to 8C are diagrams showing an example of the frame region and changes of average $\Delta CD$ in Embodiment 1. In FIG. 8A, an example of the image of the whole inspection region 10 of the target object 101 is shown. In FIG. 8B, a portion of the inspection region 10 is shown. In FIG. 8C, a graph obtained by plotting in the x direction the average $\Delta CD$ value of a plurality of frame images in, for example, the 528-th inspection stripe positioned in the image shown in FIG. 8B is shown. In FIG. 8C, the horizontal axis is shown by setting the left end of the image shown in FIG. 8B as x=0. It is evident, as shown in FIG. 8C, that the average ΔCD value does not change so abruptly even if there exists a small change (shift) between neighboring frames. However, it is evident that the average ΔCD value of the frame image in the position of x=19 or so changes abruptly when compared with neighboring frame images. Such a frame region in which the average ΔCD value changes abruptly when compared with surrounding frame images indicates the existence of many edge pairs of patterns causing a CD error when compared with surrounding frames or the existence of an edge pair of a large CD error. Conversely, a small change of the average ΔCD value between neighboring frame images indicates that the probability of the existence of a pattern causing a CD error is small. Thus, in Embodiment 1, a frame region in which the average ΔCD value changes abruptly when compared with neighboring frame images is extracted as a specific frame.

As the inclination operation process (S116), the inclination operation unit 60 operates a rate of change (inclination) of the average value from the relevant frame region to neighboring frame regions. The inclination is, for example, suitably operated for eight surrounding frames surrounding the relevant frame region. More specifically, each inclination of two frame regions continuing in the x direction and each inclination of two frame regions continuing in the y direction are determined. For the inclination in the x direction, the average value (average ΔCD) of black portions in the x direction is used. Similarly, the average value (average ΔCD) of white portions in the x direction is used. For the inclination in the Y direction, the average value (average ΔCD) of black portions in the y direction is used. Similarly, the average value (average ΔCD) of white portions in the y direction is used.

As the specific frame extraction process (S120), the extraction unit 62 extracts a specific frame from a plurality of frame regions by using the average value (average ΔCD value) to compare the relevant frame region with surrounding frame regions thereof.

Figure 9:
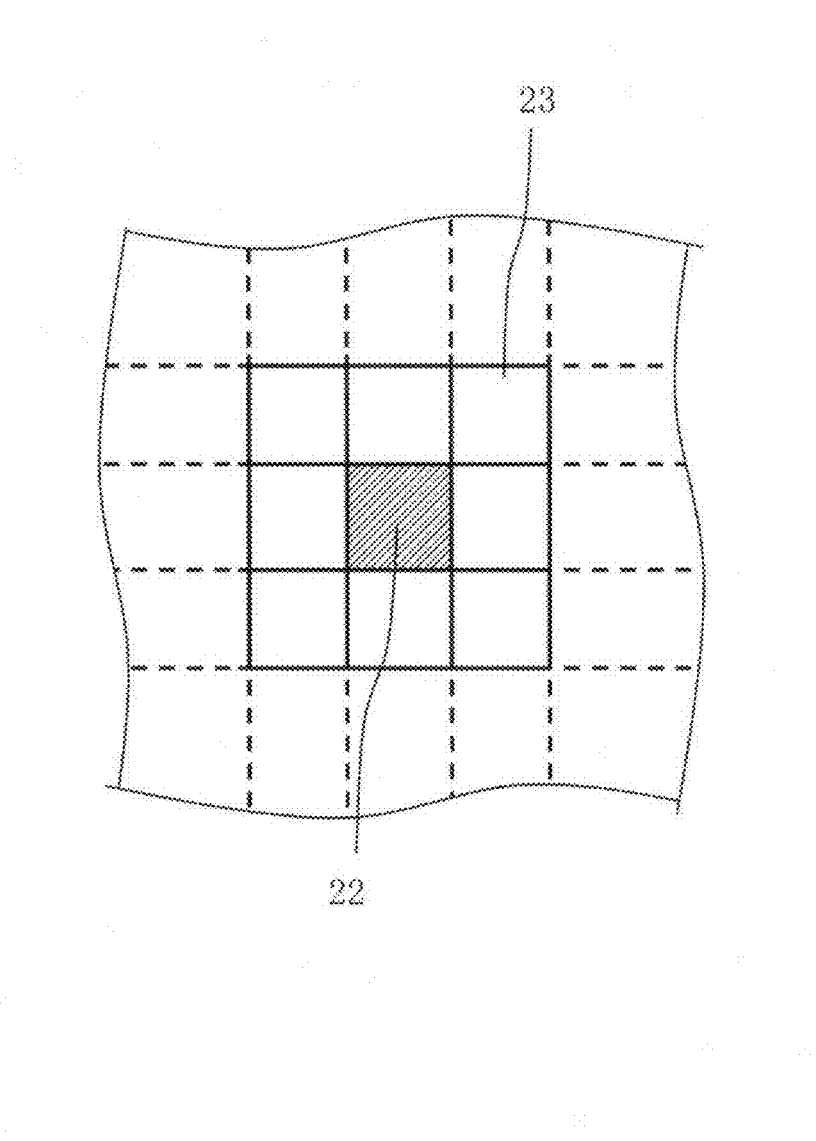
FIG. 9 is a diagram illustrating a specific frame extraction method in Embodiment 1.

FIG. 9 is a diagram illustrating a specific frame extraction method in Embodiment 1. In the specific frame extraction, more specifically, as shown in FIG. 9, a specific frame is extracted by comparing the frame region 22 with the eight surrounding frames 23 surrounding the frame region 22. More specifically, a frame region whose average rate of change (inclination) of the average value from the frame region to a neighboring frame region is equal to a threshold or more is extracted as a specific frame. When comparing with eight surrounding frames surrounding the relevant frame region, the frame region is suitably extracted as a specific frame if, for example, at least one inclination is equal to the threshold or more. Two neighboring frame regions may both be specific frames and thus, an omission (extraction omission) can be avoided or reduced by comparing with eight surrounding frames surrounding the relevant frame region. In addition, an omission (extraction omission) can further be avoided or reduced by comparing both of black portions and white portions. For example, a frame region where the average ΔCD value changes abruptly shown in FIG. 8C described above will be extracted.

As the CD inspection process (S122), the CD comparison unit 64 inspects a specific frame for CD errors (dimensional defects) of linewidth dimensions of a plurality of figure patterns in the specific frame. Because the inspection target is limited to specific frames from the whole inspection region 10 of the target object 101, the target range can be narrowed down. Therefore, the CD comparison unit 64 makes the inspection threshold stricter (smaller) than in the past and compares ΔCD and the inspection threshold for each edge pair to determine CD of the edge pair exceeding the threshold as a CD error. The threshold conventionally set to, for example, 10 nm or more can be set to a value less than 10 nm, for example, 3 nm or 5 nm by narrowing the number of frames. A determination result is stored in the memory 63. An inspection result is output to, for example, the magnetic disk drive 109, the magnetic tape drive 115, the FD 116, the CRT 117, the pattern monitor 118, or the printer 119. Alternatively, the inspection result may be output to the outside.

The average ΔCD is suitably defined for an average ΔCD map obtained by dividing the whole inspection region 10 into a plurality of frame regions and output to the magnetic disk drive 109, the magnetic tape drive 115, the FD 116, the CRT 117, the pattern monitor 118, or the printer 119. Alternatively, the inspection result may be output to the outside. Accordingly, an x direction average ΔCD map for black portions, a y direction average ΔCD map for black portions, an x direction average ΔCD map for white portions, and a y direction average ΔCD map for white portions are each created and output. The user and the like can visually check changes of the average ΔCD by viewing such maps.

According to Embodiment 1, as described above, thanks to statistical processing, the inspection region can be narrowed down to specific frame regions in which the probability that a pattern causing a CD error is arranged is high. Therefore, a CD error inspection can be conducted with high precision while making the determination threshold stricter.

Embodiment 2

In Embodiment 1, a specific frame is extracted by using the rate of change (inclination) of the average value from a frame region to a neighboring frame region, but the extraction method is not limited to such an example. In Embodiment 2, a configuration in which a specific frame is extracted by another method will be described. The configuration of the inspection apparatus 100 according to Embodiment 2 is the same as in FIG. 1.

Figure 10:
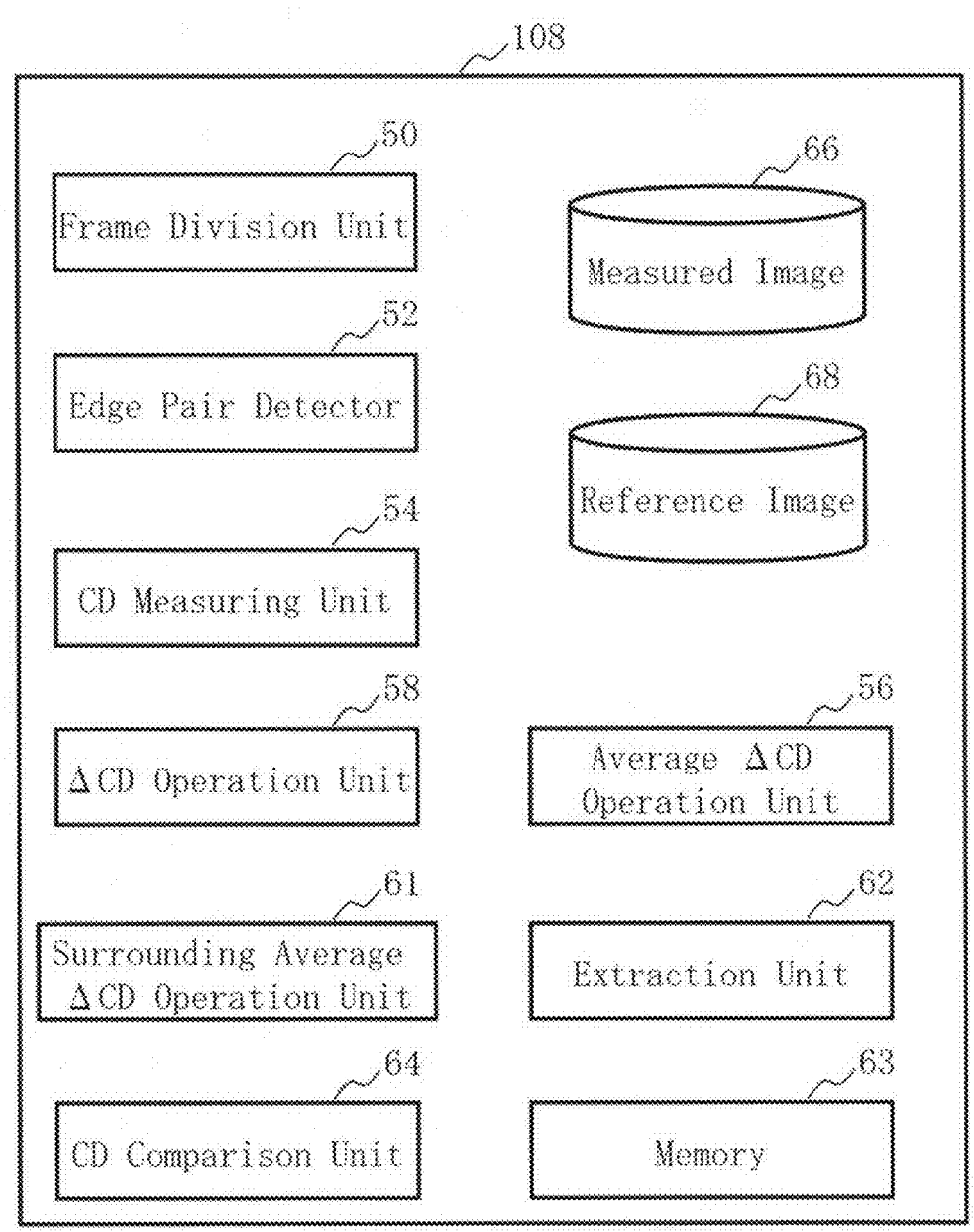
FIG. 10 is a diagram showing the internal configuration of the comparator according to Embodiment 2.

FIG. 10 is a diagram showing the internal configuration of the comparator according to Embodiment 2. FIG. 10 is the same as FIG. 2 except that, instead of the inclination operation unit 60, a surrounding average ΔCD operation unit 61 is arranged in the comparator 108. The function like that of the surrounding average ΔCD operation unit 61 may also be configured as software like a program. Alternatively, such functions may be configured by hardware such as an electronic circuit. Alternatively software and hardware may be combined.

Figure 11:
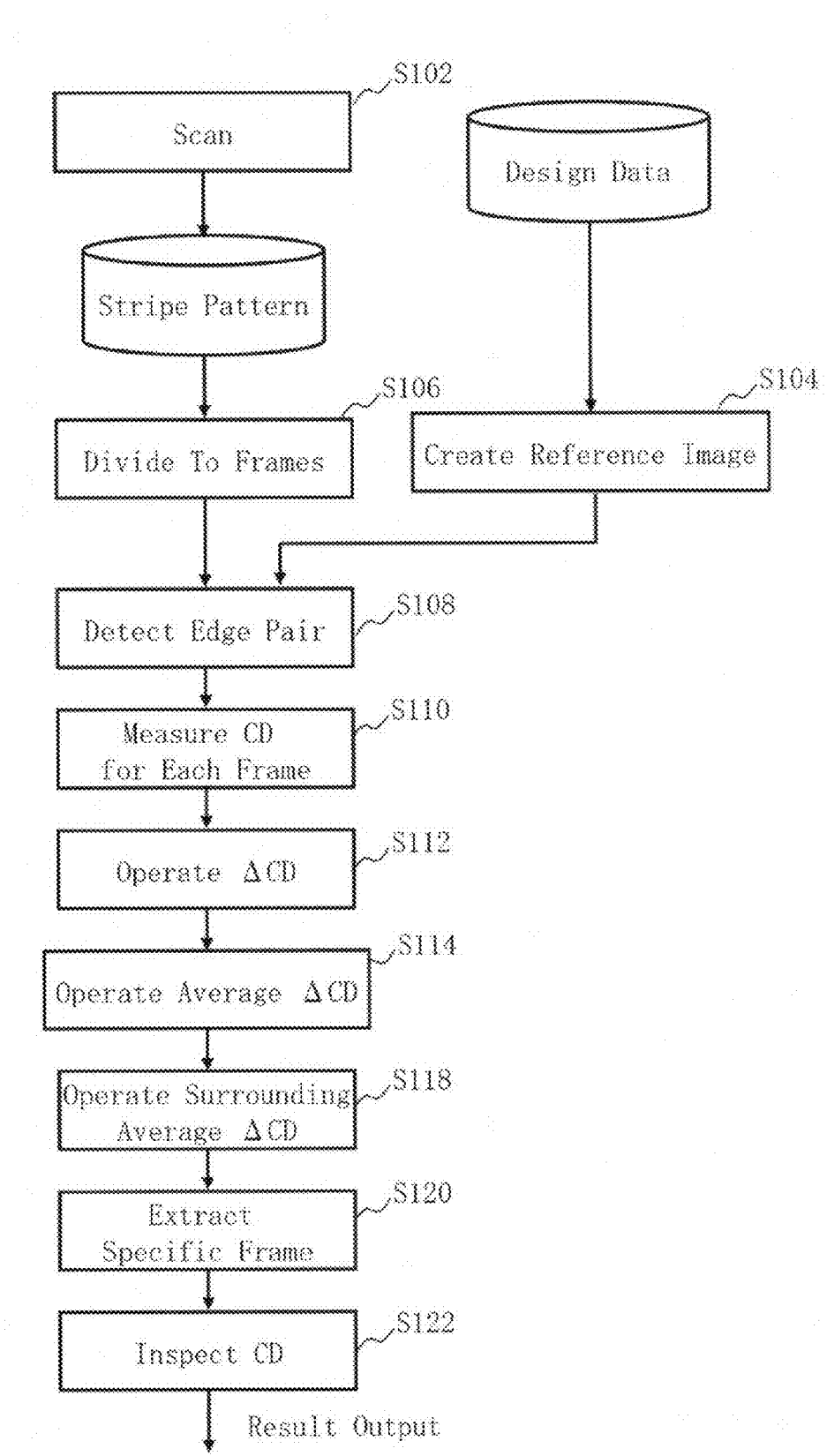
FIG. 11 is a flow chart showing principal processes of the pattern inspection method according to Embodiment 2.

FIG. 11 is a flow chart showing principal processes of the pattern inspection method according to Embodiment 2. In the pattern inspection method according to Embodiment 2, FIG. 11 is the same as FIG. 3 except that, instead of the inclination operation process (S116), a surrounding average ΔCD operation process (S118) is executed. The contents not specifically described below are the same as those in Embodiment 1.

In the surrounding average ΔCD operation process (S118), the surrounding average ΔCD operation unit 61 operates an average value (average ΔCD) of each linewidth dimension shift ΔCD (linewidth difference) between the relevant frame region and a plurality of frame regions around the relevant frame region as a whole. More specifically, the average value (average ΔCD) for each frame region is already determined and thus, the average ΔCD is added for the relevant frame region and the plurality of frame regions around the relevant frame region as a whole to determine the average value thereof. For example, the average ΔCD of each of, for example, a total of 10,000 frame regions of 100×100 (x, y directions) at the center or near the center (center portion) of the relevant frame region is added and to operate the average value thereof. The range of frame regions to be added is not 10,000 frame regions described above. At least the relevant frame region and neighboring eight surrounding frame regions surrounding the relevant frame region are used. For the surrounding average ΔCD, the surrounding average ΔCD of black portions in the x direction is determined. Similarly, the surrounding average ΔCD of black portions in the y direction is determined. Similarly, the surrounding average ΔCD of white portions in the x direction is determined. Similarly, the surrounding average ΔCD of white portions in the y direction is determined. In this manner, the surrounding average ΔCD for the relevant frame region and the plurality of frame regions around the relevant frame region as a whole is determined.

As the specific frame extraction process (S120), the extraction unit 62 extracts a frame region in a case that a difference of average value (average ΔCD) and the average value (surrounding average ΔCD) of each linewidth dimension shift of the whole surrounding is equal to the threshold or more when compared with the average value (surrounding average ΔCD) of each linewidth dimension shift of the whole surrounding as a specific frame.

According to Embodiment 2, as described above, thanks to statistical processing using the average value, the inspection region can be narrowed down to specific frame regions in which the probability that a pattern causing a CD error is arranged is high. Therefore, a CD error inspection can be conducted with high precision while making the determination threshold stricter.

Embodiment 3

In Embodiments 1 and 2, a specific frame is extracted by comparing the target frame region with surrounding frame regions, but the extraction method is not limited to such a method. In Embodiment 3, a configuration in which whether the relevant frame region is a specific frame is determined by using statistical data inside the respective frame region will be described. The configuration of the inspection apparatus 100 according to Embodiment 3 is the same as in FIG. 1.

Figure 12:
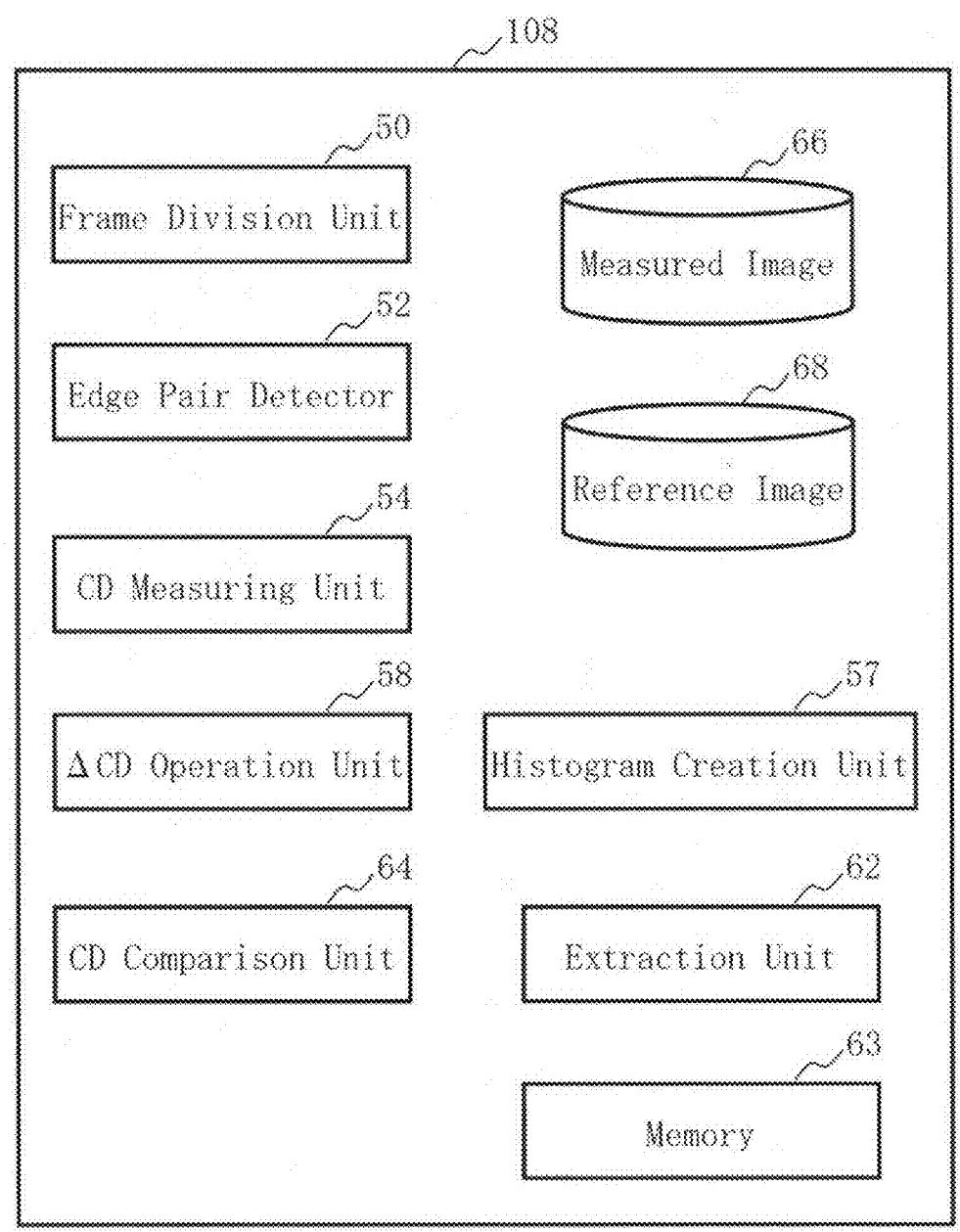
FIG. 12 is a diagram showing the internal configuration of the comparator according to Embodiment 3.

FIG. 12 is a diagram showing the internal configuration of the comparator according to Embodiment 3. FIG. 12 is the same as FIG. 2 except that, instead of the inclination operation unit 60 and the average ΔCD operation unit 56, a histogram creation unit 57 is arranged in the comparator 108. The function like that of the histogram creation unit 57 may also be configured as software like a program. Alternatively, such functions may be configured by hardware such as an electronic circuit. Alternatively software and hardware may be combined.

Figure 13:
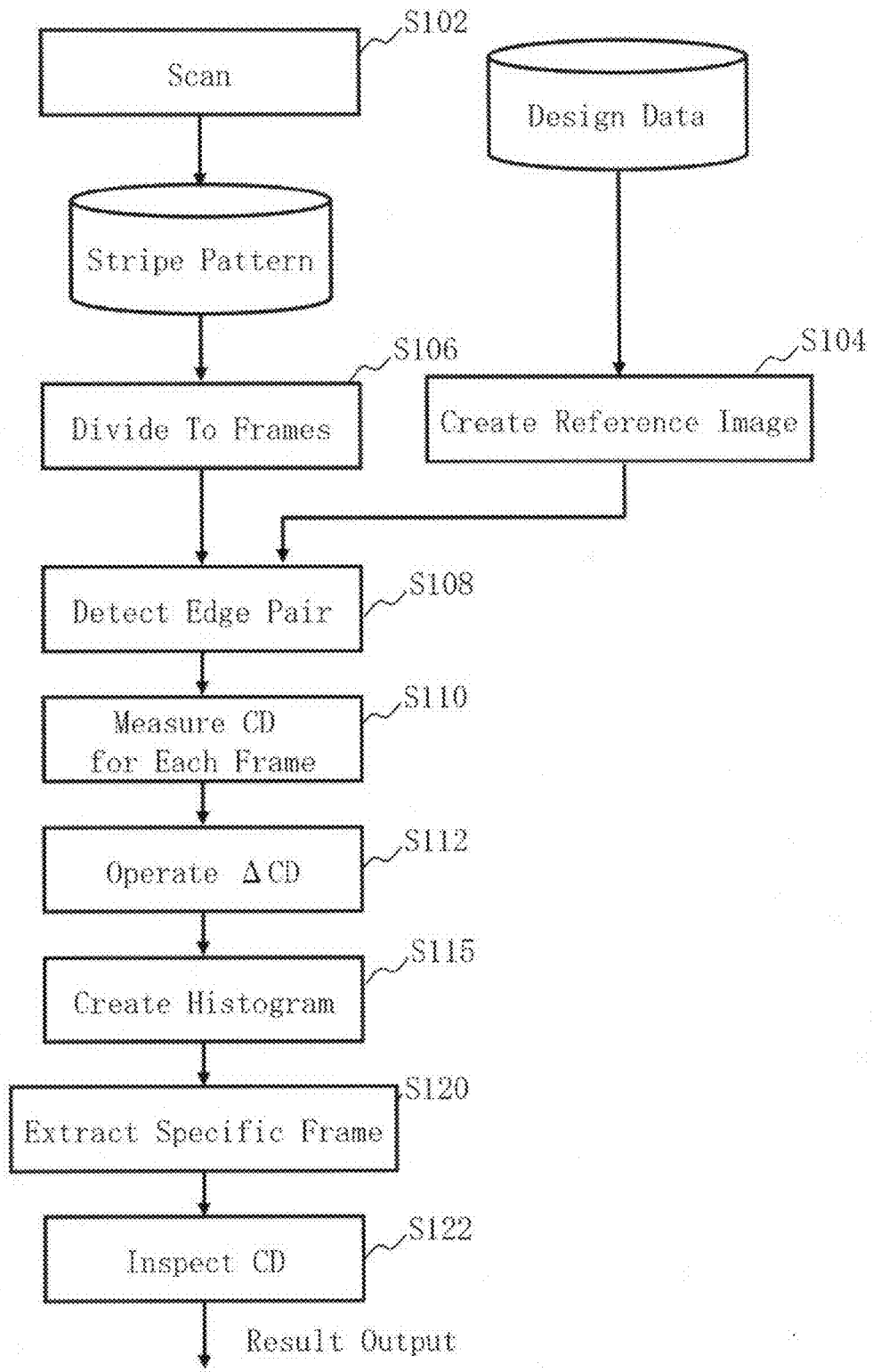
FIG. 13 is a flow chart showing principal processes of the pattern inspection method according to Embodiment 3.

FIG. 13 is a flow chart showing principal processes of the pattern inspection method according to Embodiment 3. In the pattern inspection method according to Embodiment 3, FIG. 13 is the same as FIG. 3 except that, instead of the average ΔCD operation process (S114) and the inclination operation process (S116), a histogram creation process (S115) is executed. The contents not specifically described below are the same as those in Embodiment 1.

As the histogram creation process (S115), the histogram creation unit 57 creates a histogram of each linewidth dimension shift ΔCD (linewidth difference) between linewidth dimensions of a plurality of figure patterns in a reference image corresponding to each frame region and linewidth dimensions of a plurality of figure patterns in a frame image of the frame region. In other words, the histogram creation unit 57 creates a histogram of each linewidth dimension shift ΔCD (linewidth difference) of a plurality of figure patterns in a frame image for each frame region.

Figure 14:
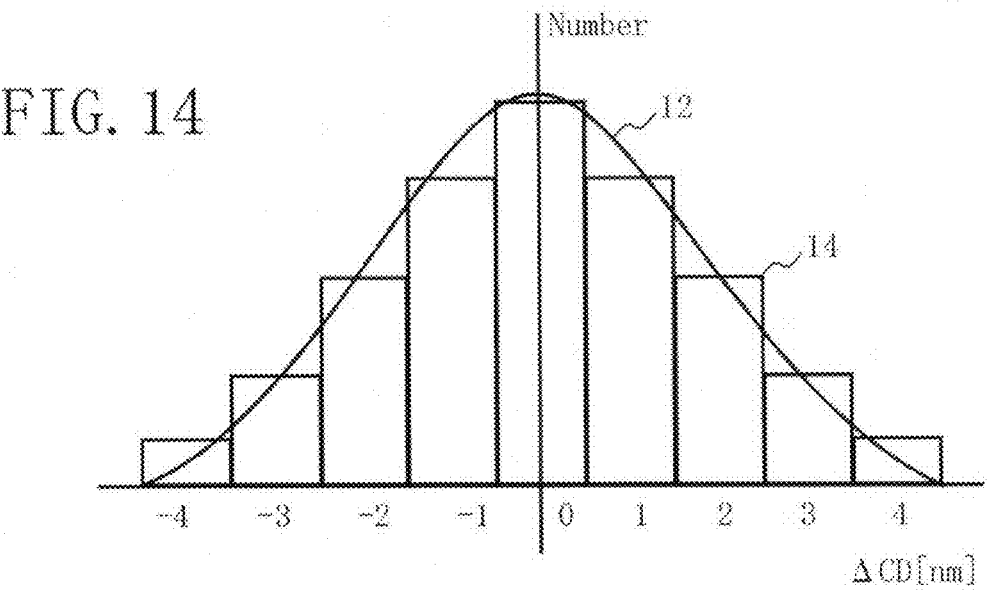
FIG. 14 is a diagram showing an example of a histogram in Embodiment 3.

FIG. 14 is a diagram showing an example of the histogram in Embodiment 3. In a histogram, the rank with the highest frequency (number) is set in the center and a plurality of vertical bars 14 constituting the histogram normally represents, as shown in FIG. 14, a normal distribution 12. In FIG. 14, the vertical axis represents the number (frequency) of ΔCD values and the horizontal axis represents the ΔCD value (rank). Normally, the ΔCD value frequently takes on 0 and as the ΔCD value increases as an absolute value, the number thereof frequently decreases. Thus, as shown in FIG. 14, for example, ΔCD=0 is set in the center and ΔCD=1 nm, 2 nm, 3 nm, . . . spread horizontally in the positive and negative directions. Alternatively, the configuration is such that a histogram showing the normal distribution is shifted to the left or right as a whole. For example, ΔCD=1 nm is set in the center and ΔCD=2 nm, 3 nm, and ΔCD=1 nm, 0 nm, −1 nm, −2 nm, . . . spread horizontally in the positive and negative directions, respectively. For such a histogram, a histogram of black portions in the x direction is created. Similarly, a histogram of black portions in the y direction is created. Similarly, a histogram of white portions in the x direction is created. Similarly, a histogram of white portions in the y direction is created. In this manner, histograms for each frame region are created.

As the specific frame extraction process (S120), the extraction unit 62 extracts a frame region for which a histogram having a linewidth dimension shift amount ΔCD (linewidth difference) deviating from the normal distribution is created from a plurality of frame regions as a specific frame.

Figure 15:
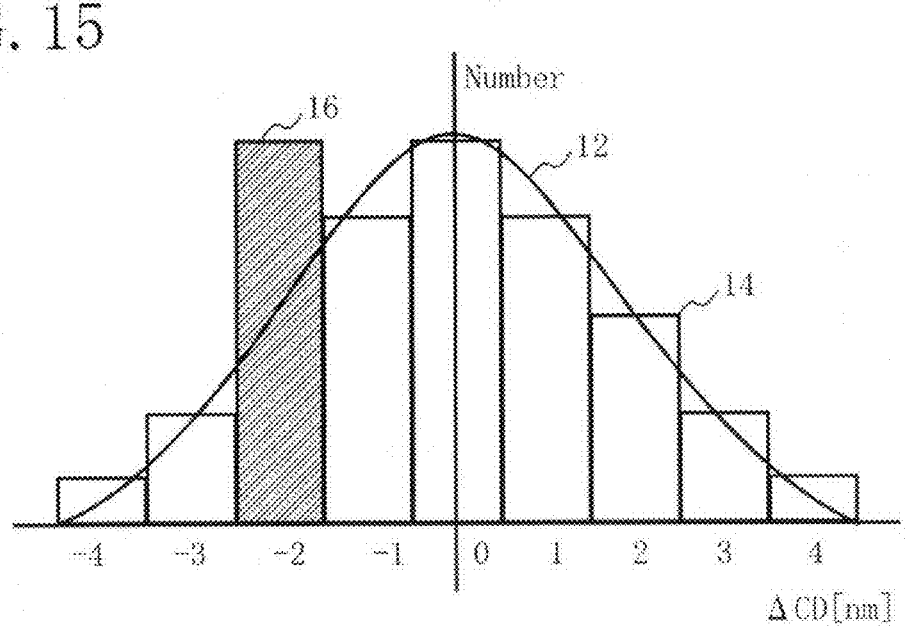
FIG. 15 is a diagram showing another example of the histogram in Embodiment 3.

FIG. 15 is a diagram showing another example of the histogram in Embodiment 3. In the histogram of FIG. 15, a case in which, among the plurality of vertical bars 14 constituting the histogram, a vertical bar 16 at ΔCD=−2 nm projects is shown. In FIG. 15, a case in which the vertical bar 16 projects on the inner side of the foot (end portion) of the normal distribution is shown.

Figure 16:
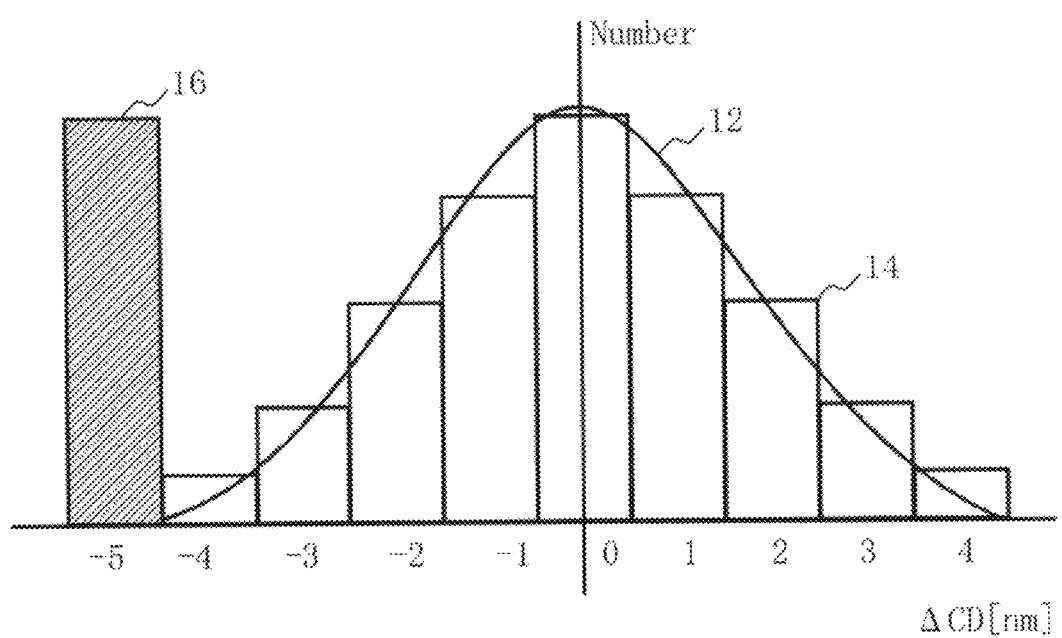
FIG. 16 is a diagram showing still another example of the histogram in Embodiment 3.

FIG. 16 is a diagram showing still another example of the histogram in Embodiment 3. In the histogram of FIG. 16, a case in which, among the plurality of vertical bars 14 constituting the histogram, the vertical bar 16 at ΔCD=−5 nm projects is shown. In FIG. 16, a case in which the vertical bar 16 projects on the outer side of the foot (end portion) of the normal distribution is shown.

If, even if there is a case of a large value of ΔCD, a histogram shows the normal distribution, such a large value can statistically be interpreted as a measurement error. Conversely, a histogram in which the vertical bar 16 projecting by deviating from the normal distribution arises can be interpreted, instead of a simple measurement error, to indicate the existence of many edge pairs causing a CD error. Thus, a frame region constituting a histogram in which the vertical bar 16 projecting by deviating from the normal distribution as shown, for example, in FIG. 15 or FIG. 16 indicates from the statistical viewpoint the existence of many edge pairs causing a CD error. Thus, the existence of a pattern causing a CD error is indicated. Conversely, a frame region constituting a histogram showing the normal distribution indicates from the statistical viewpoint that the probability of the existence of a pattern causing a CD error is low including a case in which a histogram showing the normal distribution shifted to the left or right as a whole instead of setting the center value as ΔCD=0 is constituted. Thus, in Embodiment 3, a frame region from which a histogram having ΔCD deviating from the normal distribution is created is extracted as a specific frame.

In Embodiment 3, as described above, whether the relevant frame region is a specific frame is determined by using statistical data inside the respective frame region.

Also according to Embodiment 3, as described above, the inspection region can be narrowed down to specific frame regions in which a pattern causing a CD error is likely to be arranged based on statistical processing using a histogram. Therefore, a CD error inspection can be conducted with high precision while making the determination threshold stricter. In the example of FIG. 16, for example, if the threshold is set to 10 nm by conventionally assuming a CD inspection of the whole inspection region 10, "−5 nm" shown in FIG. 16 will not be detected as a CD error. Here, however, the existence of ΔCD of "−5 nm" deviating from the normal distribution is known and ΔCD can be detected as a CD error by setting the threshold to 4 nm.

A case of transferring a 1:1 line & space pattern whose half pitch HP is 12 nm by double patterning using an optical system whose reduction ratio from a mask to a wafer is 4 times is assumed. The pixel size is set to, for example, 50 nm and a frame region is formed from 512×512 pixels. The whole frame region is assumed to be a line & space pattern. It is also assumed that the length of a defective pattern to be detected is 500 nm and a CD error of the length is 3.5 nm, and pattern writing noise (edge roughness) is ±2 nm (3σ). In such a case, HP is 12 nm and 4 times reduction ratio is achieved by double patterning and thus, 12 nm×4×2×2=192 nm is obtained. The vertical and horizontal size of an image of the frame (512×512 pixels) is (50×512) nm, the number of monochrome lines & spaces is (50×512)/192 and this is measured for each line and thus, the number of calculated positional shifts of each of black and white portions is approximately 68267 (68267≈512×(512×50)/192. In a defective pattern (ΔCD=3 nm) of the length 500 nm, 500/50≈10 edge pairs exist for each of black and white portions. When a histogram is created in increments of 1 nm, if the normal distribution is followed when edge roughness is ±2 nm (3σ), the number of pieces of data in the range of 0 to 1 nm is 29573 (1.5σ), the number of pieces of data in the range of 1 to 2 nm is 4472 (1.5σ to 3σ), the number of pieces of data in the range of 2 to 3 nm is 86 (3σ to 4.5σ), and the number of pieces of data in the range of 3 nm or more is 2. Thus, the number of pieces of data in the range of +3 to +4 nm of black portions is around 2 if there is no defect and the normal distribution is followed. Because about 10 edge pairs of a CD error to be detected are present, the error is adequately detectable as a feature point.

In the above description, a " . . . circuit" or a " . . . process" can be configured by hardware such as an electronic circuit. Alternatively, such a " . . . circuit" or a " . . . process" can be configured by a program that can be operated on a computer. Alternatively, such a " . . . circuit" or a " . . . process" may be implemented not only by a program to be software, but also by a combination of hardware and software, or may be combined with firmware. When configured by a program, the program is recorded a record carrier body such as a magnetic disk drive, magnetic tape drive, FD, or ROM (Read Only Memory). For example, the table control circuit 114, the expansion circuit 111, the reference circuit 112, and the comparator 108 configuring an operation controller may be configured by an electric circuit or may be realized by software that can be processed by the control computer 110. Alternatively, such circuits may be realized by combining an electric circuit and software.

In the foregoing, the embodiments have been described with reference to concrete examples. However, the present invention is not limited to such concrete examples. In the embodiments, for example, a transmitted illumination optical system using transmitted light is shown as the illumination optical system 170, but the illumination optical system is not limited to such an example. For example, a reflected illumination optical system using reflected light may be used. Alternatively, transmitted light and reflected light may be used simultaneously by combining a transmitted illumination optical system and a reflected illumination optical system.

Parts of the apparatus configuration, the control method, and the like which are not needed to be explained directly for the explanation of the present invention are not described. However, a necessary apparatus configuration and a necessary control method can be appropriately selected and used. For example, the configuration of a control unit that controls the inspection apparatus 100 is not described, but it is needless to say that a necessary control unit configuration is appropriately selected and used.

In addition, all pattern inspection apparatuses and pattern inspection methods including the elements of the present invention and whose design can appropriately be altered by those skilled in the art are included in the scope of the present invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A pattern inspection method comprising:
   acquiring, with a pattern inspection apparatus, a plurality of optical images regarding a plurality of figure patterns arranged in each of a plurality of frame regions obtained by virtually dividing an inspection region of a target object, for each of the plurality of frame regions;
   measuring with the pattern inspection apparatus, linewidth dimensions of the plurality of figure patterns in an optical image of the plurality of optical images regarding a frame region concerned, for each of the plurality of frame regions;
   operating, with the pattern inspection apparatus, an average value of each linewidth dimension shift between linewidth dimensions of a plurality of figure patterns in a reference image corresponding to the frame region concerned and the linewidth dimensions of the plurality of figure patterns in the optical image regarding the frame region concerned, for each of the plurality of frame regions;
   extracting, with the pattern inspection apparatus, a specific frame from the plurality of frame regions by comparing the average value of the frame region concerned, with average values of frame regions around the frame region concerned, for each of the plurality of frame regions; and
   inspecting, with the pattern inspection apparatus, the specific frame for dimensional defects of linewidth dimensions of a plurality of figure patterns arranged in the specific frame.

2. The method according to claim 1, wherein a frame region whose rate of change of the average value from the frame region concerned to neighboring frame regions is equal to a threshold or more is extracted as the specific frame.

3. The method according to claim 1, wherein the specific frame is extracted by comparing eight surrounding frames surrounding the frame region concerned and the frame region concerned, for each of the plurality of frame regions.

4. The method according to claim 1, further comprising: operating an average value of each linewidth dimension shift regarding the frame region concerned and the frame regions around the frame region concerned as a whole,
wherein the frame region concerned in a case that a difference of average value of the frame region concerned and the average value of each linewidth dimension shift as the whole is equal to a threshold or more when compared with the average value of each linewidth dimension shift as the whole is extracted as the specific frame.

5. The method according to claim 1, further comprising: creating the reference image corresponding to the optical image of the frame region concerned for each of the plurality of frame regions.

6. The method according to claim 5, further comprising: detecting an edge portion of each of the plurality of figure patterns in the optical image to be paired with the edge portion of each of a plurality of figure patterns in the corresponding reference image for each of the plurality of optical images of the plurality of frame region.

7. The method according to claim 6, further comprising: measuring each linewidth dimension shift of the linewidth dimensions of the plurality of figure patterns in the optical image corresponding to the frame region concerned for each of the plurality of frame regions.

8. The method according to claim 7, further comprising: operating each linewidth dimension shift between linewidth dimensions of the plurality of figure patterns in the reference image corresponding to the frame region concerned and the linewidth dimensions of the plurality of figure patterns in the optical image regarding the frame region concerned for each of the plurality of frame regions.

9. The method according to claim 1, further comprising: operating a rate of change of the average value from the frame region concerned to neighboring frame regions.

10. A pattern inspection method comprising:
acquiring, with a pattern inspection apparatus, an optical image of a plurality of figure patterns arranged in each of a plurality of frame regions obtained by virtually dividing an inspection region of a target object for each of the plurality of frame regions;
measuring, with the pattern inspection apparatus, linewidth dimensions of the plurality of figure patterns in the optical image regarding a frame region concerned for each of the plurality frame regions;
creating, with the pattern inspection apparatus, a histogram of linewidth dimension shift using each linewidth dimension shift between linewidth dimensions of a plurality of figure patterns in a reference image corresponding to the frame region concerned and the linewidth dimensions of the plurality of figure patterns in the optical image regarding the frame region concerned for each of the plurality frame regions;
extracting, with the pattern inspection apparatus, a frame region for which a histogram having a linewidth dimension shift amount deviating from a normal distribution is created as a specific frame from the plurality of frame regions; and
inspecting, with the pattern inspection apparatus, the specific frame for dimensional defects of the linewidth dimensions of a plurality of figure patterns arranged in the specific frame.

11. The method according to claim 10, further comprising: creating the reference image corresponding to the optical image regarding the frame region concerned for each of the frame regions.

12. The method according to claim 11, further comprising: detecting an edge portion of each of the plurality of figure patterns in the optical image to be paired with the edge portion of each of a plurality of figure patterns in the corresponding reference image for each of the plurality of optical images of the plurality of frame region.

13. The method according to claim 12, further comprising: measuring each linewidth dimension shift of the linewidth dimensions of the plurality of figure patterns in the optical image corresponding to the frame region concerned for each of the plurality of frame regions.

14. The method according to claim 13, further comprising: operating each linewidth dimension shift between linewidth dimensions of the plurality of figure patterns in the reference image corresponding to the frame region concerned and the linewidth dimensions of the plurality of figure patterns in the optical image regarding the frame region concerned for each of the plurality of frame regions.

15. The method according to claim 10, further comprising: operating a rate of change of the average value from the frame region concerned to neighboring frame regions.

16. The method according to claim 2, wherein the specific frame is extracted by comparing eight surrounding frames surrounding the frame region concerned and the frame region concerned, for each of the plurality of frame regions.

* * * * *